United States Patent [19]

Lukasavage et al.

[11] Patent Number: 5,268,469

[45] Date of Patent: Dec. 7, 1993

[54] PROCESS OF MAKING IMPACT INSENSITIVE ALPHA-HMX

[75] Inventors: William Lukasavage, Succasunna; Steven Nicolich, Saddle Brook; Jack Alster, Fair Lawn, all of N.J.

[73] Assignee: The United States of America as represented by the Secretary of the Army, Washington, D.C.

[21] Appl. No.: 956,811

[22] Filed: Oct. 2, 1992

Related U.S. Application Data

[63] Continuation of Ser. No. 775,407, Oct. 15, 1991, abandoned.

[51] Int. Cl.$^5$ .............................................. C07D 257/02
[52] U.S. Cl. .................................................... 540/475
[58] Field of Search ......................... 149/92, 105, 106; 540/475; 568/924

[56] References Cited

U.S. PATENT DOCUMENTS

| | | | |
|---|---|---|---|
| 2,959,587 | 11/1960 | Johnson et al. | 540/475 |
| 3,239,502 | 3/1966 | Lee et al. | 540/475 |
| 3,304,300 | 2/1967 | Watters | 540/475 |
| 3,351,585 | 11/1967 | Lee et al. | 540/475 |
| 3,939,148 | 2/1976 | Siele et al. | 540/475 |
| 4,925,936 | 5/1990 | Levinthal | 540/475 |

*Primary Examiner*—Robert L. Stoll
*Assistant Examiner*—John M. Covert
*Attorney, Agent, or Firm*—Anthony T. Lane; Edward Goldberg; Michael C. Sachs

[57] ABSTRACT

An improved process of making a highly impact insensitive form of HMX called Alpha HMX has been accomplished. Test results of insensitive impact from drop heights of 5 to 10 times greater than Beta HMX, the conventional explosive, has been successfully achieved. This accomplishment has been achieved without the addition of any additives, and is attributed to the attainment of small particle size, whole crystals, narrow size distribution, and sample purity.

3 Claims, No Drawings

PROCESS OF MAKING IMPACT INSENSITIVE ALPHA-HMX

GOVERNMENTAL INTEREST

The Government has rights in this invention pursuant to Contract No. DAAA21-86-C-0171 awarded by the Department of the Army.

The invention described herein was made in the course of, or under, a contract or subcontract thereunder with the Government and may be manufactured, used and licensed by or for the Government for Governmental purposes without the payment to us of any royalties thereon.

This application is a continuation, of application Ser. No. 07/775,407, filed Oct. 15, 1991 now abandoned.

FIELD OF USE

This invention relates to an improved method of making Alpha-HMX which is highly impact insensitive.

BACKGROUND OF THE INVENTION

HMX, which is known as 1,3,5,7-tetranitro-1,3,5,7-tetraazacyclooctane, is the most powerful non-atomic explosive in military use. However, widespread use of this explosive has been limited by its excessive cost. Although HMX was first discovered in 1941, the only known process for its manufacture is the Bachmann Process but this is limited in its industrial applicability. The latter process has only been demonstrated in batch mode, and requires large excesses of reagents.

In spite of the difficulties of production, and the resulting high price, HMX has gained wide reputation as the most powerful nitramine explosive. In fact, HMX is the undisputed benchmark for all other explosives.

HMX would be applied more widely, however, if two short comings could be overcome, viz. The price of the material, and its impact sensitivity.

The first of these problems has been eliminated. The second problem has been attempted to be solved by various formulations, and compositions, all of which sought to modify its sensitivity through the inclusion of additives, both active and inert.

HMX has four polymorphs viz. Alpha, Beta, Gamma, and Delta. Three of these are stable enough to be prepared, and isolated. Delta is the only one of the four, which is unstable enough in the explosive art to be of no significance. Only trace amounts of this polymorph have been prepared for analytical purposes. Long standing reports clearly indicate that only the Beta polymorph should be considered useful, and safe. It is useful because of its high density, and safe because of its lack of sensitivity to shock. The literature indicates that Alpha and Gamma HMX are comparable to lead azide in terms of its shock sensitivity, and therefore are dangerous.

The most recent attempts to reduce the shock sensitivity of HMX have centered upon the use of small particle size in combination with additives. In the art, Beta HMX having an average particle size of 5 microns is known as Class 5 Beta HMX.

SUMMARY OF INVENTION

It is an object of this invention to provide an improved process of making HMX which provides both high power, and extreme insensitivity, at a price which competes directly with the less expensive nitramines analog RDX.

Another object is to provide an improved process of making Alpha HMX which is less sensitive to impact than Beta HMX itself. In fact, this process which produces Alpha HMX having an insensitivity to impact from drop heights of 5 to 10 times greater than that of Beta HMX itself. With this polymorph available at reasonable cost, it is expected that it could be used as a substitute for Beta HMX in existing formulations. This would provide insensitivity to the most conventional high powered explosive known to date.

Other objects and the attendant advantages of this invention will become more evident from a reading of the following specification:

DESCRIPTION OF EMBODIMENTS

The special insensitivity of this HMX is due to several factors, each of which must be held in tight tolerance. The particle size must be kept to about 1 to about 5 micron in range, the polymorph must be alpha, and the purity must be very high. To obtain the right polymorph the amount of nitric acid used must be carefully controlled as too high or too low a dilution could cause the formation of gamma HMX. Further, the temperature of the reaction must be kept as close to room temperature as possible because if the temperature rises above 45 degrees Centigrade, the product again obtained is gamma HMX, instead of alpha HMX, the desired product. To obtain the right size, the product must be precipitated with great agitation in the manner described with a high speed mixing turbine at about 15,000 RPM. The purity of the product must be upgraded using the solid phase up-grading techniques hereinafter described. Failure to follow any and all of the steps in the procedure, may seriously compromise, if not prevent the establishment of the special property of insensitivity to this alpha HMX material.

EXAMPLE 1

Nitration of TAT with a mixture of nitric acid and phosphorous pentoxide.

250 grams, within the effective range of 200 to 300 grams, of 98% nitric acid were introduced into a 500 ml. beaker, provided with a thermometer, and a magnetic stirring bar. 70 grams of phosphorous pentoxide were then added in portions over a 30 minute period. The addition was made with stirring via the magnetic stirring bar and the rate of addition of the phosphorous pentoxide was dictated by the temperature of the reaction mixture, which was not permitted to rise above 35 degrees Centigrade. The reaction mixture was allowed to stir covered by a piece of aluminum foil until the temperature fell to room temperature. 50 grams of TAT were then added in about 4 equal portions at such a rate that the temperature was prevented from rising above 40 degrees Centigrade. The reaction mixture was allowed to fall to room temperature, and the stirring bar was removed when all signs of any exothermic action had subsided. The beaker was covered by aluminum foil and allowed to set undisturbed for 16 hours at room temperature. During this time the entire reaction mixture sets-up to a cream cheese like consistency.

The reaction mixture is discharged directly into the vortex of a room temperature water bath stirred by an L-TEC air turbine mixed, (see U.S. Pat. No. 4,424,677), specifically designed for very high speed mixing and dispersing. The water acts to brake the reaction complex, and precipitates the alpha HMX, guaranteeing the formation of extremely small particles (crystals). The solid crude alpha is filtered, and washed with as much cold water as necessary to reach a constant of 7 ph. (This water should be maintained between 10 to 35 degrees Centigrade to prevent any digestion of the size of the crystals. The filtered but damp cake is then dispersed in 6 to 8 times its mass of agitated boiling water. The total washing time should not exceed 2 minutes in order to prevent size enhancement via digestion. The washed crude HMX, which should have no odor, is then filtered hot, and rinsed with cold water. This curtails crystal digestion before being thoroughly dried. The drying may be simple air drying, or vacuum drying at a temperature near 50 degrees Centigrade.

The still crude HMX must now be up-graded in purity before use. This is accomplished by anyone of the following methods.

PART 2

METHOD A

Purification of the contaminated HMX produced above by trituration with a nitric acid/phosphorous pentoxide mixture.

100 grams of the contaminated HMX are added portion wise to 100 grams of nitric acid (about 70 ml.), within the effective range 80 to 120 grams, containing 12.5 grams, which is within effective range 10 to 14 grams, of phosphorous pentoxide. The container may be a simple beaker which may be covered with aluminum foil. The quantity of nitric acid used here may be increased (not above 130 grams) for easier mixing of the mixture. The quantity used here has been found to be given about as thick a mixture as is practical. The quantity of phosphorous pentoxide may be reduced or increased depending for the greater part upon the amount of water originally present in the nitric acid and the amount of SEX present in the sample. The quantities used here have been found to work well over a very wide range of sample purities with initial melting points as low as 230 degrees centigrade. The phosphorous pentoxide should be fully dissolved and contain no solid particles. The nitric acid may be prepared ahead of time and kept as a stock solution. The HMX must be free of DANNO (1,5-diacetyloctahydro-3-nitro-7-nitroso-1,3,5,7-tetraazocine), since contamination with this compound can cause dangerous fume-offs. The gradual addition of the HMX to the nitric acid solution is to facilitate the mixing as no exothermic action should occur. The paste is left for about 16 hours at room temperature, samples may be taken to determine completion of the reaction. Reactions have been intentionally left for several days to determine if any danger results. No decomposition or fume-offs have resulted from this even when the reactions were allowed to completely dry out. When the reaction is complete the paste is spooned out of the container and dispersed in water. The HMX is washed at the filter with water until the ph remains constant. The HMX is then boiled in 8 times its weight of water for a few minutes to remove any residual phosphoric acid. The boiling continues until any foam on top has disappeared. If sufficient water is not used this foam will persist, and more water should be used. When the foam has broken up the dried material will have a literature melting of about 282 degrees centigrade which indicates a purity of greater than 98%.

METHOD B

The quantities and methods as in Example 1 above, however, a water proof container is employed and the mixture is placed in a constant temperature bath at 40 degrees centigrade. The thickness of the paste in the container is limited so as to permit attainment of bath temperature throughout the mixture in a reasonable period of time. If necessary the mixture may be stirred mechanically. Under these conditions the upgrading time is reduced to approximately 4 hours.

METHOD C

The same quantities were used as set forth in Example 1 however, the mixture is fed through a heated screw mixer or feeder for rapid mixing and temperature equilibration. The temperature may be adjusted upwards to the 70 degree region reducing the reaction time to a matter of minutes.

RESULTS

The impact values obtained via the "ERL, Type 12 Impact Tester" using a 2 and one half kilogram mass, demonstrated values 5 to 10 times greater than normally achievable with "Class 5 Beta HMX", and kinetic energy values 10 to 20 times greater than normal, As the following actual data indicates

| DROP | Initiation y = yes, n = no |
| --- | --- |
| 100 cm drop | n |
| 100 cm drop | n |
| 100 cm drop | n |
| 100 cm drop | n |
| 100 cm drop | n |
| 100 cm drop | n |
| 100 cm drop | n |
| 100 cm drop | n |
| 100 cm drop | n |
| 100 cm drop | n |
| 150 cm drop | n |
| 150 cm drop | n |
| 150 cm drop | y |
| 150 cm drop | n |
| 150 cm drop | n |
| 150 cm drop | y |
| 150 cm drop | n |
| 150 cm drop | y |
| 150 cm drop | n |
| 150 cm drop | y |

Do to the damage being caused to the test apparatus by the large amount of kinetic energy released from such great drop heights it was decided to accept the 50% initiation value as being somewhere above 150 cm.

ANALYSIS

We have found that small crystals of Alpha HMX, which were produced by this process, have an average particle size of about 1 to about 5 microns are remarkably resistant to impact initiation. Using the standard impact test (ERL, Type 12 impact tester), the 50% initiation point was found to be greater than 150 cm. This is a tremendously higher value than Beta HMX (Class 5) which has a 50% initiation point of 35 cm when examined by the same test method. It should be noted that the 150 cm value, cited above, is also much higher than many explosives normally considered relatively insensitive such as TNT which has 61.3 cm point. See Table below.

TABLE 1

| EXPLOSIVES | IMPACT 50% PT (CM) |
|---|---|
| HMX | 35.0 ± 1.8 |
| RDX | 39.0 ± 1.3 |
| PETN | 17.1 ± 2.2 |
| TNT | 61.3 ± 2.1 |
| COMP B | 44.2 ± 3.4 |
| ALPHA HMX | 150 |

CONCLUSION

The practice of the present invention is considered to be novel. The prior art attempts to achieve high levels of insensitivity of Alpha HMX or Beta HMX have had no success. What little progress that has been made is at the price of diluting the performance of the material Beta HMX with the incorporation of foreign substances.

This invention provides extreme insensitivity of Alpha HMX without compromising purity, and does this by the unique application of the present invention to change the dangerously sensitive alpha polymorph of HMX to a highly insensitive polymorph. We maintain very tight particle distribution of Alpha HMX within about 1 to about 5 microns.

In summary, this process proceduces the most powerful but least sensitive non-atomic exlosive in existence today. The explosive is the purest HMX known, and it contains no RDX contamination.

The foregoing disclosure and drawings are merely illustrative of the principles of this invention and are not to be interpreted in a limiting sense. We wish it is to be understood that We do not desire to be limited to the exact details described because obvious modifications will occur to a person skilled in the art.

We claim:

1. In an improved method of producing improved alpha 1,3,5,7-tetranitro-1,3,5,7-tetrazacyclooctane (HMX), which is pure alpha HMX having a particle distribution between about 1 and about 5 microns thereby producing a highly insensitive alpha HMX for use as a conventional high energetic compound, the improvement consisting essentially of adding HMX contaminated with 1-Aceto-3,5,7-trinitro-1,3,5,7-tetraazacyclooctane to a nitric acid and phosphoric pentoxide solution to facilitate mixing thereby producing a paste, allowing said paste to stand at about 22° to 45° C. degrees Centigrade for at least 16 hours, dispersing said paste in water, filtering, and washing until the pH remains constant, and finally boiling at about 100 to 102 degrees Centigrade said HMX in about 8 times its weight of water to remove residual contamination indicated by the disappearance of any foam.

2. The method of claim 1 wherein said paste is a mass maintained by agitation at about 40 to 45 degrees Centigrade throughout said mass thereby ungrading said alpha HMX in about 30 minutes to 4 hours.

3. The method of claim 2 wherein said paste is then rapidly mixed, and said temperature is further allowed to rise to about 45 degrees Centigrade thereby reducing said alpha HMX upgrading to 30 minutes.

* * * * *